(12) United States Patent
Fong et al.

(10) Patent No.: US 11,754,567 B2
(45) Date of Patent: Sep. 12, 2023

(54) CANCER DETECTION AND ABLATION SYSTEM AND METHOD

(71) Applicant: City of Hope, Duarte, CA (US)

(72) Inventors: Yuman Fong, Duarte, CA (US); Michael Storrie-Lombardi, Duarte, CA (US); Veronica Jones, Duarte, CA (US); Daniel Schmolze, Duarte, CA (US); Lily L. Lai, Duarte, CA (US); Ragini Kothari, Duarte, CA (US)

(73) Assignee: City of Hope, Duarte, CA (US)

( * ) Notice: Subject to any disclaimer, the term of this patent is extended or adjusted under 35 U.S.C. 154(b) by 169 days.

(21) Appl. No.: 17/051,681

(22) PCT Filed: Apr. 30, 2019

(86) PCT No.: PCT/US2019/029998
§ 371 (c)(1),
(2) Date: Oct. 29, 2020

(87) PCT Pub. No.: WO2019/213133
PCT Pub. Date: Nov. 7, 2019

(65) Prior Publication Data
US 2021/0231662 A1 Jul. 29, 2021

Related U.S. Application Data

(60) Provisional application No. 62/664,518, filed on Apr. 30, 2018.

(51) Int. Cl.
G01N 33/574 (2006.01)
G16H 50/20 (2018.01)
(Continued)

(52) U.S. Cl.
CPC ........... *G01N 33/574* (2013.01); *A61B 18/20* (2013.01); *G01N 21/658* (2013.01); *G01N 33/54346* (2013.01); *G06N 3/08* (2013.01); *G16H 50/20* (2018.01); *A61B 2018/00577* (2013.01); *A61B 2018/00642* (2013.01);
(Continued)

(58) Field of Classification Search
CPC ............... G01N 33/574; G01N 21/658; G01N 33/54346; G01N 2201/06113; G16H 50/20; A61B 18/20; A61B 2018/00577; A61B 2018/00642; A61B 2018/00702; A61B 2018/00773; A61B 2018/2005; G06N 3/08
See application file for complete search history.

(56) References Cited

U.S. PATENT DOCUMENTS 6,975,898 B2 * 12/2005 Seibel .................. A61B 1/07
                                                    600/478
9,877,655 B2 * 1/2018 Huang ................. G02B 23/26
(Continued)

Primary Examiner — Shirley X Jian
(74) Attorney, Agent, or Firm — Mintz Levin Cohn Ferris Glovsky and Popeo, P.C.

(57) ABSTRACT

Systems and methods are configured to detect and/or ablate cancerous tissue, such as during surgery. The system uses Laser Ramen Spectroscopy (LRS) or Surface Enhanced Raman Spectroscopy (SERS) to enhance a detection signal pursuant to a spectroscopy analysis of tissue. Rapid in situ detection of cancer can be combined with immediate laser thermal ablation of the cancerous tissue. The detection and ablation can occur before, during, or after surgical resection.

17 Claims, 10 Drawing Sheets

(51) Int. Cl.
*A61B 18/20* (2006.01)
*G01N 21/65* (2006.01)
*G01N 33/543* (2006.01)
*G06N 3/08* (2023.01)
*A61B 18/00* (2006.01)

(52) U.S. Cl.
CPC .............. *A61B 2018/00702* (2013.01); *A61B 2018/00773* (2013.01); *A61B 2018/2005* (2013.01); *G01N 2201/06113* (2013.01)

(56) References Cited

U.S. PATENT DOCUMENTS

| | | | |
|---|---|---|---|
| 9,895,063 B1 | 2/2018 | Hannaford et al. | |
| 9,931,039 B2* | 4/2018 | Huang | A61B 5/0075 |
| 10,746,730 B2* | 8/2020 | Braeckmans | G01N 33/54346 |
| 10,888,227 B2* | 1/2021 | Kircher | A61B 1/00087 |
| 2005/0100967 A1* | 5/2005 | Leslie | G01N 33/57442 |
| | | | 435/7.1 |
| 2009/0028407 A1* | 1/2009 | Seibel | A61B 1/0627 |
| | | | 382/131 |
| 2010/0070197 A1* | 3/2010 | Wang | G01J 3/02 |
| | | | 702/22 |
| 2010/0317964 A1* | 12/2010 | Hendriks | A61B 5/6848 |
| | | | 600/567 |
| 2014/0166884 A1* | 6/2014 | Kapelushnik | G01N 21/35 |
| | | | 250/339.08 |
| 2014/0350534 A1* | 11/2014 | Kircher | A61B 5/0075 |
| | | | 606/41 |
| 2015/0011893 A1* | 1/2015 | Lui | A61B 5/7264 |
| | | | 600/476 |
| 2015/0018807 A1* | 1/2015 | Kircher | A61B 18/02 |
| | | | 606/12 |
| 2015/0185207 A1* | 7/2015 | Black | G01N 21/59 |
| | | | 435/29 |
| 2015/0335248 A1* | 11/2015 | Huang | A61B 5/0084 |
| | | | 702/19 |
| 2016/0000330 A1* | 1/2016 | Huang | G02B 23/26 |
| | | | 600/476 |
| 2017/0020460 A1* | 1/2017 | Leblond | A61B 5/4842 |
| 2017/0035399 A1* | 2/2017 | Mak | A61B 5/4887 |
| 2017/0299594 A1 | 10/2017 | Depinho et al. | |
| 2018/0047555 A1 | 2/2018 | Pringle et al. | |
| 2018/0372730 A1* | 12/2018 | Braeckmans | G01N 33/5076 |
| 2021/0231662 A1* | 7/2021 | Fong | G01N 33/54346 |

* cited by examiner

CANCER DETECTION AND ABLATION SYSTEM AND METHOD

CROSS-REFERENCE TO RELATED APPLICATIONS

This application is a national stage application filed under 35 U.S.C. § 371, of International Patent Application No. PCT/US2019/029998, filed Apr. 30, 2019, which claims priority to U.S. Provisional Patent Application No. 62/664,518, filed Apr. 30, 2018, entitled "CANCER DETECTION AND ABLATION SYSTEM AND METHOD", the contents of which are hereby incorporated by reference in their entirety.

BACKGROUND

Surgical resection is a process by which a cancer tissue is surgically removed from a patient in order to remove or reduce the spread of the cancerous disease. One possible goal during surgery is to remove cancerous tissue along with a rim of normal tissue around the cancerous tissue so as to increase the likelihood that all of the cancer has been removed.

A resection margin or surgical margin is the margin of apparently non-tumerous tissue around a tumor that has been surgically removed. The resection is an attempt to remove a cancer tumor so that no portion of the malignant growth extends past the edges or margin of the removed tumor and surrounding tissue. Undetected cancer cells can remain in the tissue margin after surgery, which can be detrimental to the patient.

There is a need for improved systems and methods for detection and/or ablation of cancer cells in tissue prior to, during, or after surgery or detection of cancerous tissue.

SUMMARY

Disclosed are systems and methods for detecting and/or ablating cancer cells in a patient, such as prior to, during, or after surgery. In an example implementation, Spectroscopy (such as laser Raman spectroscopy (LRS)) is used to identify and/or collect spectra from tissue of a patient, such as from both healthy and malignant tissue. An analysis is then performed that provides an indication of the likelihood of the tissue containing cancer. The systems and methods employ a graphical user interface to enhance the process. In addition, signal enhancing systems, such as the use of gold nanoparticles (or other particles), can be used to enhance a spectroscopy signal (such as the Raman signal). In an example implementation, the disclosed systems and methods are also used pursuant to an ablation procedure to ablate tissue during surgery (or after surgery.)

Instead of, or in addition to, resection of cancerous tissue, another surgical option is to combine rapid in situ detection with immediate laser thermal ablation of the cancerous tissue. The detection and ablation can occur before, during, or after surgical resection. In this regard, the tissue is analyzed such as pursuant to Raman spectroscopy procedure to obtain a spectral signature that indicates whether or not the tissue is cancerous. If the signature indicates that cancer is present, the tissue can be immediately ablated such as via laser.

The details of one or more variations of the subject matter described herein are set forth in the accompanying drawings and the description below. Other features and advantages of the subject matter described herein will be apparent from the description and drawings, and from the claims.

DETAILED DESCRIPTION

Disclosed are systems and methods configured to detect and/or ablate cancerous tissue, such as during surgery. The system uses Laser Ramen Spectroscopy (LRS) or Surface Enhanced Raman Spectroscopy (SERS) to enhance a detection signal pursuant to a spectroscopy analysis of tissue. SERS is a surface-sensitive technique that enhances Raman scattering by molecules adsorbed on rough metal surfaces or by nanostructures such as plasmonic-magnetic silica nanotubes. Laser Raman spectroscopy (LRS) is an optical technique in surgical diagnostics. LRS harnesses the vibrational frequencies of molecular bonds to provide a unique biochemical signature for target tissues.

Pursuant to an example process, LRS is merged with an unsupervised clustering algorithm, k-means, and stochastic backpropagation artificial neural networks (ANNs) to generate real time estimates of a Bayesian probability that a breast tissue target contains cancer cells. In a non-limiting example, a panel of ANNs are all trained on Raman spectra with histopathology diagnostics that provide Bayesian estimates of the presence or absence of cancer in tissue. In an example embodiment, at least one ANN is trained on data across an entire spectral bandwidth. Additional ANNs can be utilized that specialize in the analysis of data from selected portions of the high wavenumber and fingerprint regions that are particularly sensitive to changes in nucleotide, protein, carbohydrate, and lipid cell components. The independent analyses of the additional ANNs are configured to detect mixtures of healthy and cancer tissue that are not detected by a simple one-shot full spectra analysis.

In an implementation, nanoparticles, such as gold nanoparticles, are used as a signal enhancer during the spectroscopy process, such as to enhance the Raman signal so that it can be captured more quickly. In a non-limiting example, the system is used for breast cancer detection and/or treatment. In an initial step, tissue samples from breast cancer patients are collected. Spectra from both healthy tissue and malignant tissue are also collected pursuant to a SERS process. In a non-limiting implementation, the tissue is tested at two different wavelengths, such as 785 nanometers and 1064 nanometers wavelength devices. Raman spectroscopy is used to differentiate between the two tissue types.

The collected spectra are then analyzed to provide a result for a clinician that informs a percentage likelihood of the imaged tissue containing cancer. This can be in preparation for using Raman spectroscopy clinically during surgery. In an embodiment, the system can also be used to ablate tissue based on the output and information provided from a graphical user interface.

Figure 1:
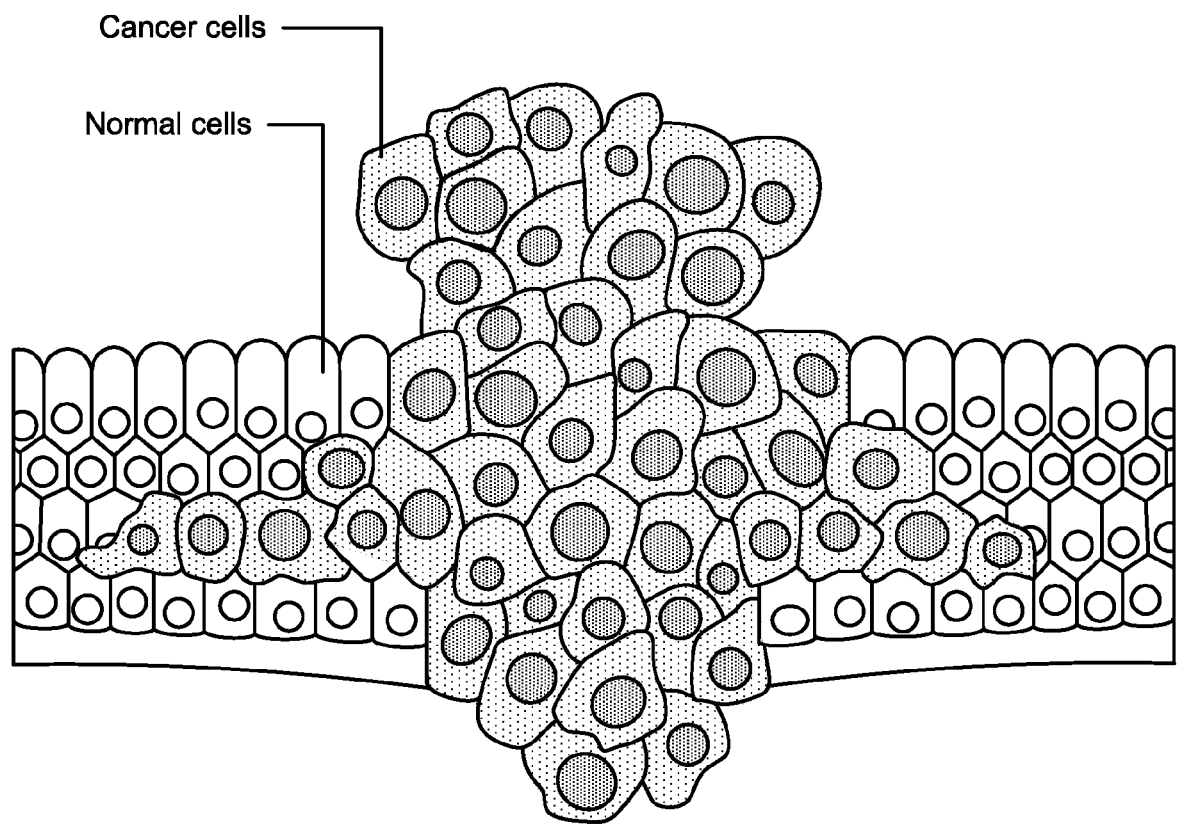
FIG. 1 shows a schematic representation of cancer cells and normal cells in tissue.
Figure 2:
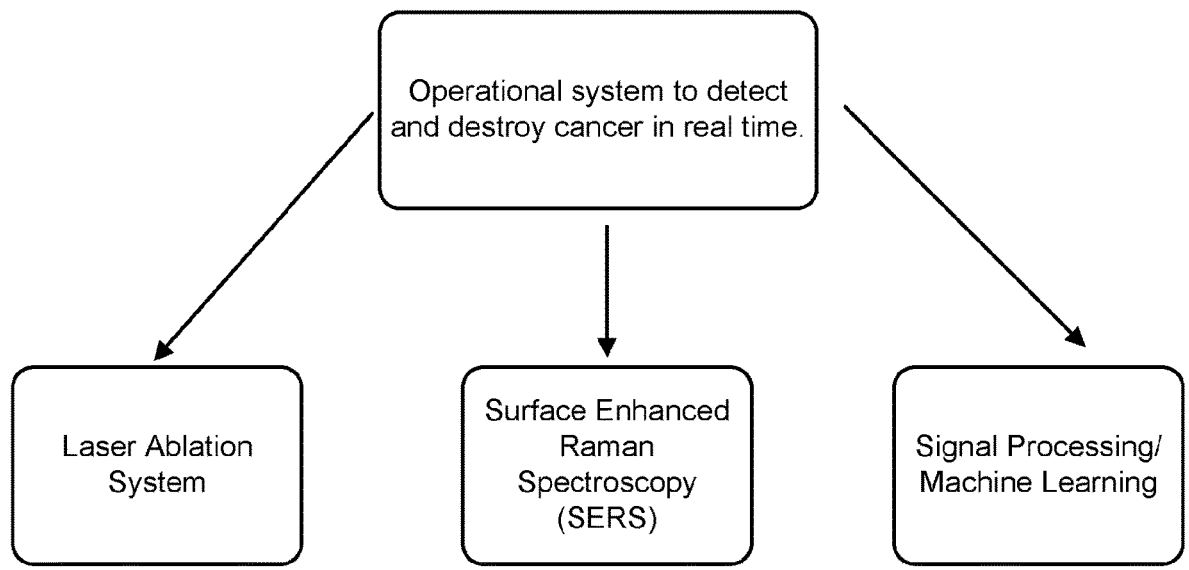
FIG. 2 shows a schematic representation of a system for detecting and/or destroying cancer cells.

FIG. 1 shows a schematic representation of cancer cells and normal cells in tissue. As mentioned, Raman spectroscopy is used to distinguish between healthy tissue and cancerous tissue. In an implementation, the cells are tested at two different wavelengths, such as 785 and 1064 wavelength devices. FIG. 2 shows a representation of a system for detecting and/or treating cancer cells, such as in real time for example. The system includes a spectroscopy system, such as a LRS or SERS system for testing tissue.

In breast cancer diagnostics, LRS can characterize microcalcifications, distinguish immortalized, transformed, and invasive breast cancer cells, and map the spatial distribution of carotenoids, mammaglobin, palmitic acid and sphingomyelin in ductal breast cancer. The spectral specificity of the Raman scattering event pursuant to LRS enables relatively quick distinction between lipid, protein, and DNA|RNA cell components. As a result, the technique can detect cellular changes characteristic of cancer tissue in vivo during the surgical procedure, facilitating real time margin evaluation.

In a non-limiting example implementation, the Raman instrumentation employes a B&W Tek 785 nm system (the i-Raman Plus.) The i-Raman Plus uses a high quantum efficiency 2048-pixel CCD array detector with a spectral resolution of 4.5 cm-1 and a spectral coverage range from 150-2250 cm-1. The detector cooled temperature is −2C.° with a typical dynamic range of 50,000:1. The effective pixel size is 14 µm×9 µm. Such a system is highly portable. The spectrometer housing connects via fiber optic cables to the BAC102 Raman Trigger Probe. The probe has a spot size of 50-85 µm. The BAC150B probe holder can be used to stabilize the probe for benchtop data collection, or the probe can be handheld during use in the surgical field. Alternatively, the probe can be integrated with a B&W Tek BAC151B video sampling system, or the BAC104 adapter can be used to integrate the probe with a standard laboratory Olympus microscope.

A signal processing system is used to analyze the spectra obtained from the SERS system and to provide one or more test results. The signal processing system can include one or more neural networks in a non-limiting example. As mentioned, the neural networks can include artificial neural networks (ANNs) that are to generate real time estimates of a Bayesian probability that a breast tissue target contains cancer cells. A panel of ANNs are all trained on Raman spectra with histopathology diagnostics provide Bayesian estimates of the presence or absence of cancer in tissue. In an example embodiment, the ANNs include at least one trained on data across an entire spectral bandwidth. Additional ANNs are utilized that specialize in the analysis of data from selected portions of the high wavenumber and fingerprint regions that are particularly sensitive to changes in nucleotide, protein, carbohydrate, and lipid cell components. The independent analyses of the additional ANNs are configured to detect mixtures of healthy and cancer tissue that are not detected by a simple one-shot full spectra analysis Based on test results, a laser ablation system can be used to destroy tissue that has been identified as cancerous.

Figure 3:
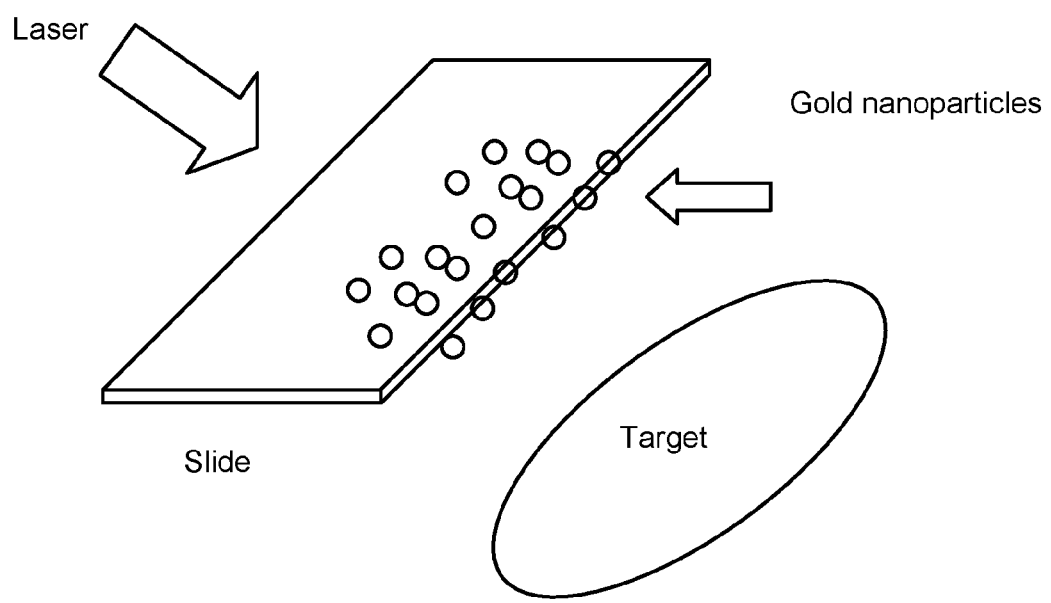
FIG. 3 shows a schematic representation of a Surface Enhanced Raman Spectroscopy (SERS) process on target tissue.
Figure 4:
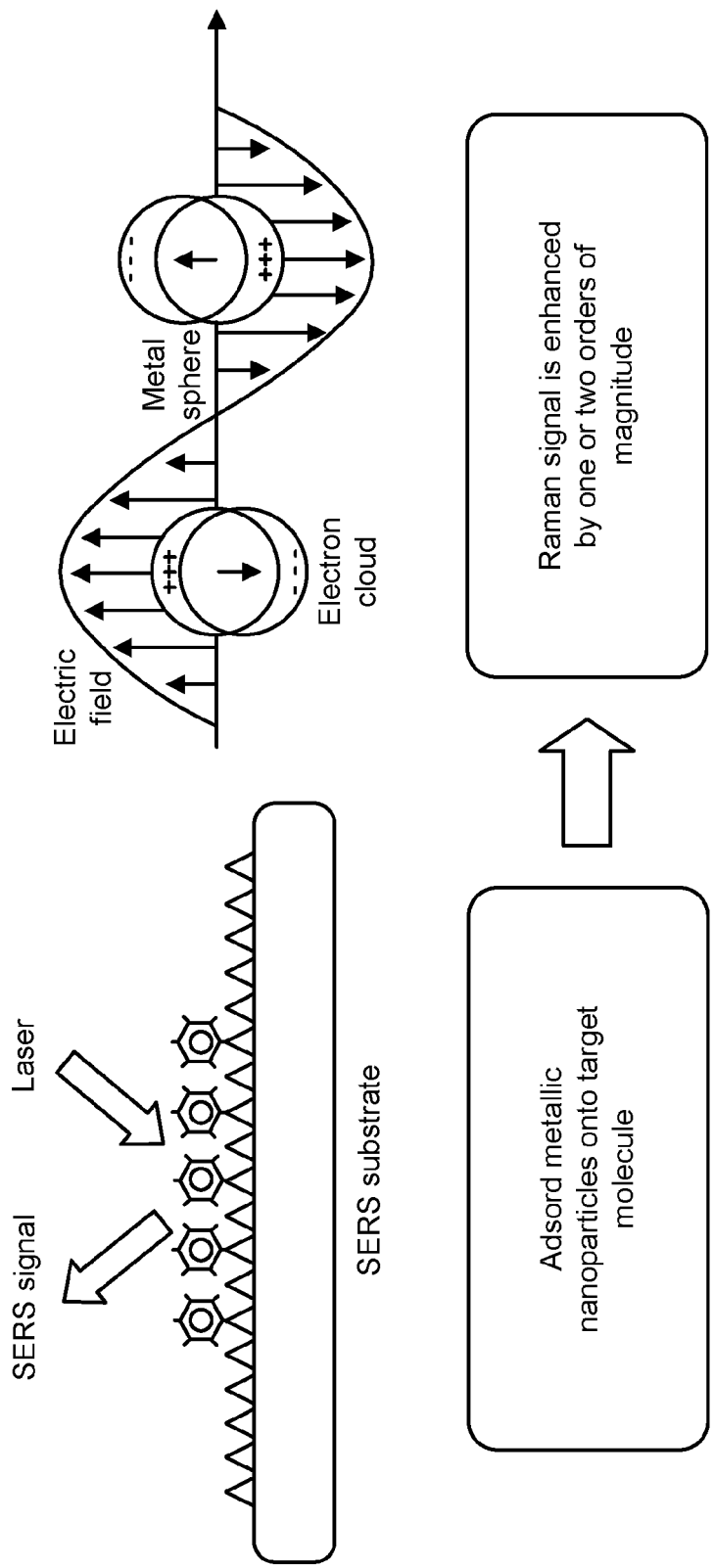
FIG. 4 shows a schematic representation of a SERS process for detecting and/or ablating cancerous tissue.

FIG. 3 shows a representation of a process for analyzing target tissue. A spectroscopy laser is applied to target tissue to obtain a signal. As mentioned, the use of gold nanoparticles (or other particles), can be used to enhance the spectroscopy signal. As shown in FIG. 4, the metallic nanoparticles are adsorbed onto a target molecule to provide a signal, such as Raman signal. The Raman signal is enhanced, such as on the order of one or two orders magnitude, by the metallic nanoparticles.

A processor is programmed with an analysis process to analyze the spectra and provide a result that informs a likelihood of the imaged tissue containing cancer. In this regard, the processor may be coupled to a user interface to provide for user interaction with the system. The processor may also include or be coupled to a neural network to enhance the analysis.

Figure 5:
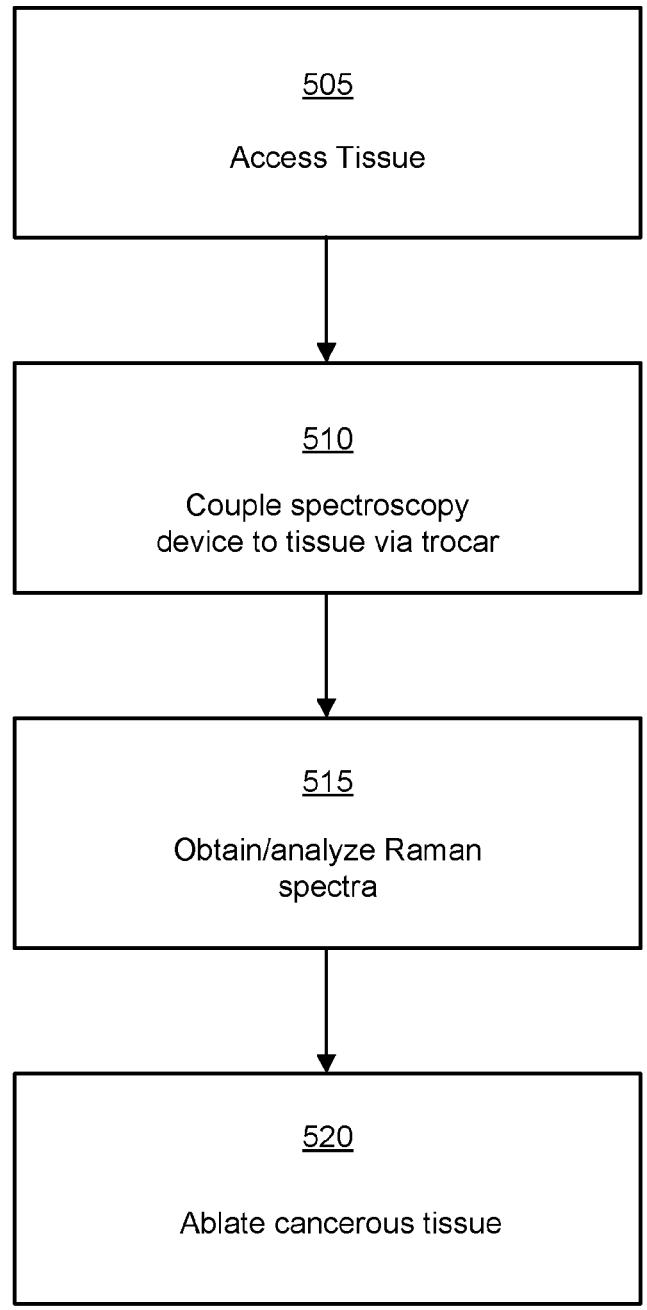
FIG. 5 shows a flow diagram of an example detection and ablation process.
Figure 6:
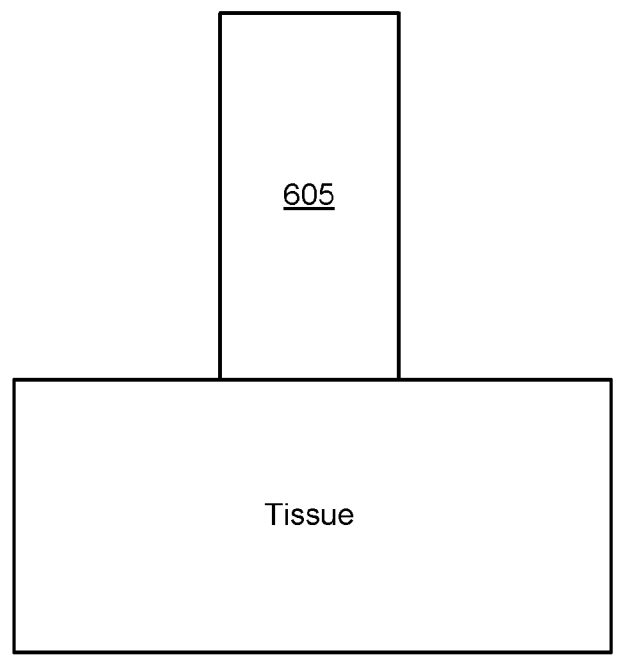
FIGS. 6 and 7 show schematic representations of tissue being accessed and analyzed.

With reference to FIG. 5, there is now described a non-limiting example method of rapid, in situ detection of cancerous tissue followed by immediate laser thermal ablation of the cancerous tissue. It should be appreciated that the ablation of tissue is not limited to laser ablation. In an initial step 505, a trocar or other access device is inserted into or otherwise coupled to the tissue to be analyzed to provide access to the tissue. The trocar can include a lumen through which an analysis device, such as a laser fiber, can be inserted into the tissue. FIG. 6 shows a schematic representation of a trocar 605 inserted into tissue 610.

Figure 7:
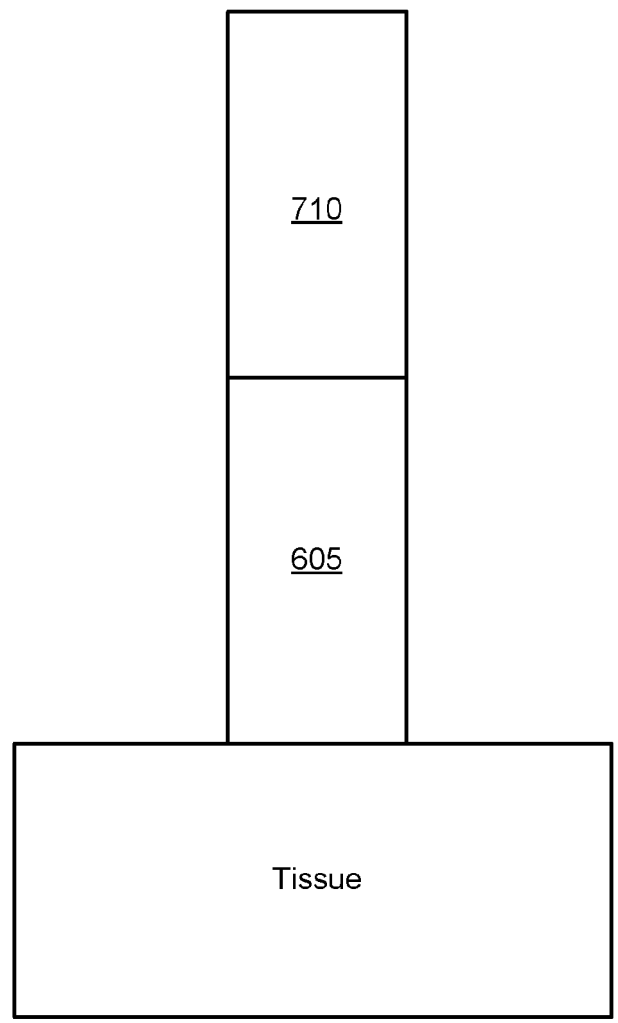
Figure 8:
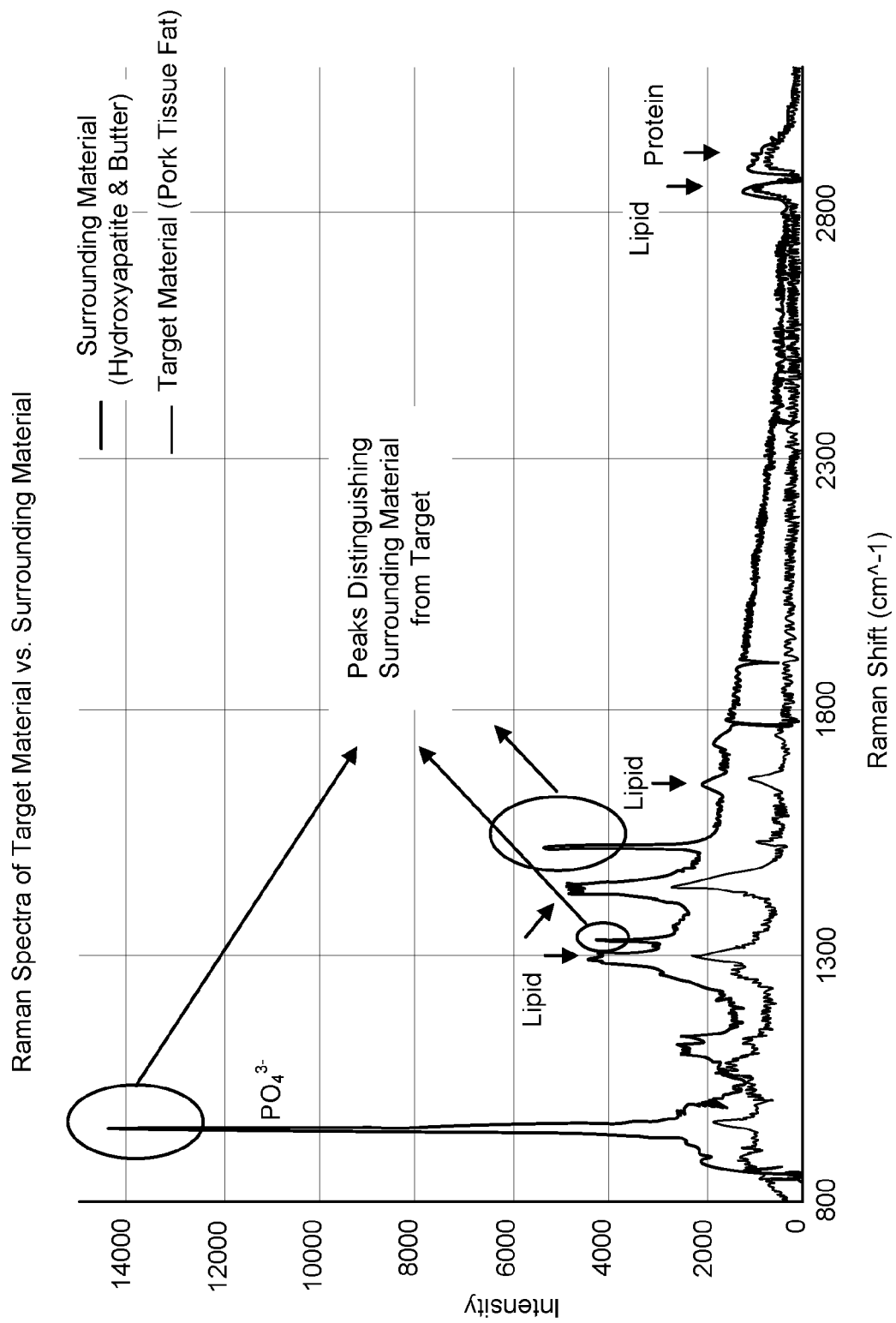
FIG. 8 shows an example Raman spectra.

In a next step 510 with reference to FIG. 5, a spectroscopy device, such as a laser fiber, is inserted into the tissue (or otherwise coupled to the tissue) by inserting the laser fiber through the trocar. FIG. 7 schematically shows the laser fiber 710 inserted into the tissue. With reference again to FIG. 5, a Raman spectra of the tissue is then obtained at step 515. The Raman spectra is then analyzed to determine whether the tissue is cancerous. FIG. 8 shows an example of a Raman spectra that indicates that an analyzed tissue is cancerous. As mentioned, one or more neural networks can be used to analyze the tissue. In addition, a graphical user interface (GUI) can be provided to provide a graphical representation in real time as to whether the tissue is cancerous.

Figure 9:
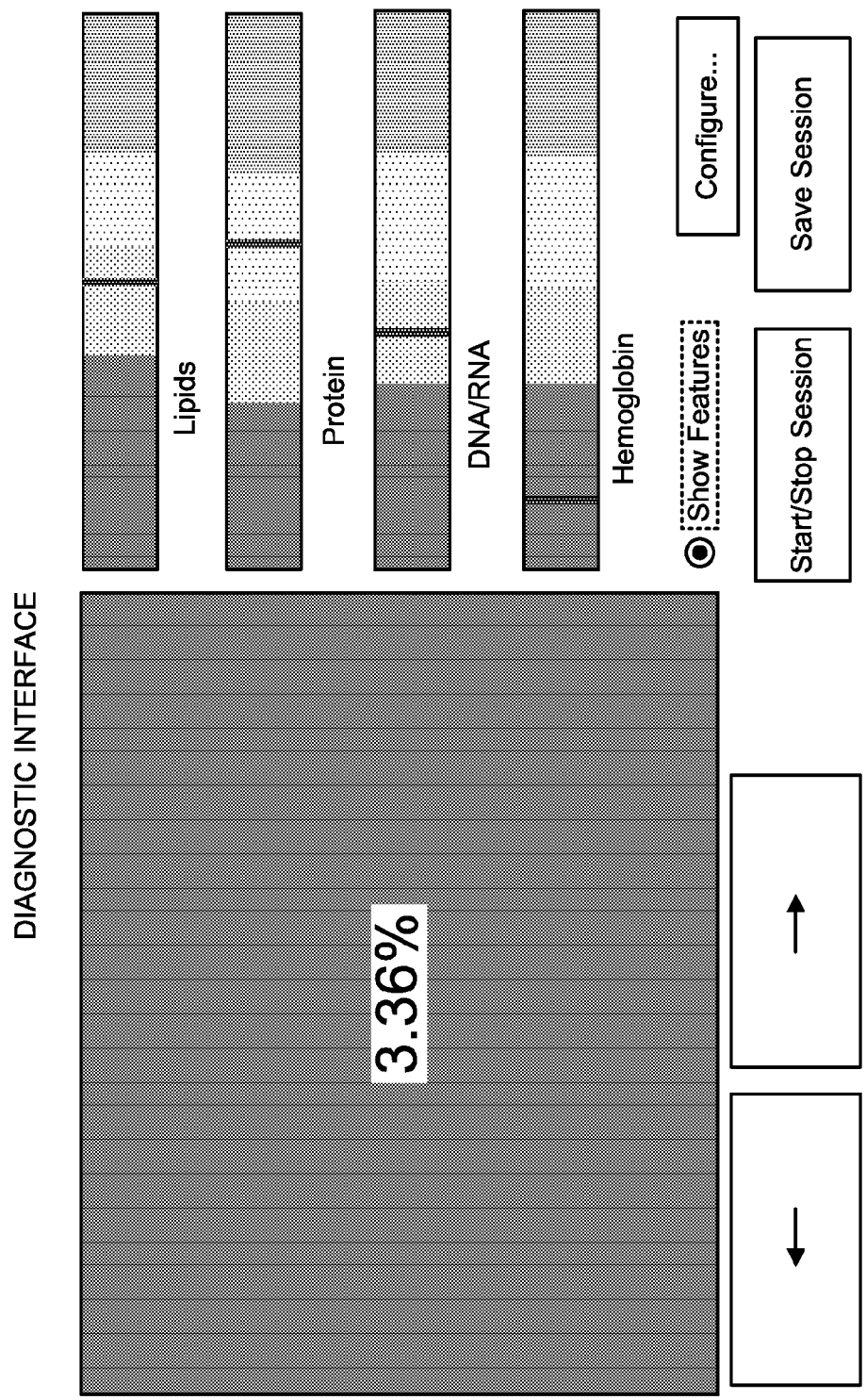
FIGS. 9 and 10 show non-limiting examples of graphical user interfaces that may be displayed or otherwise provided to a user.
Figure 10:
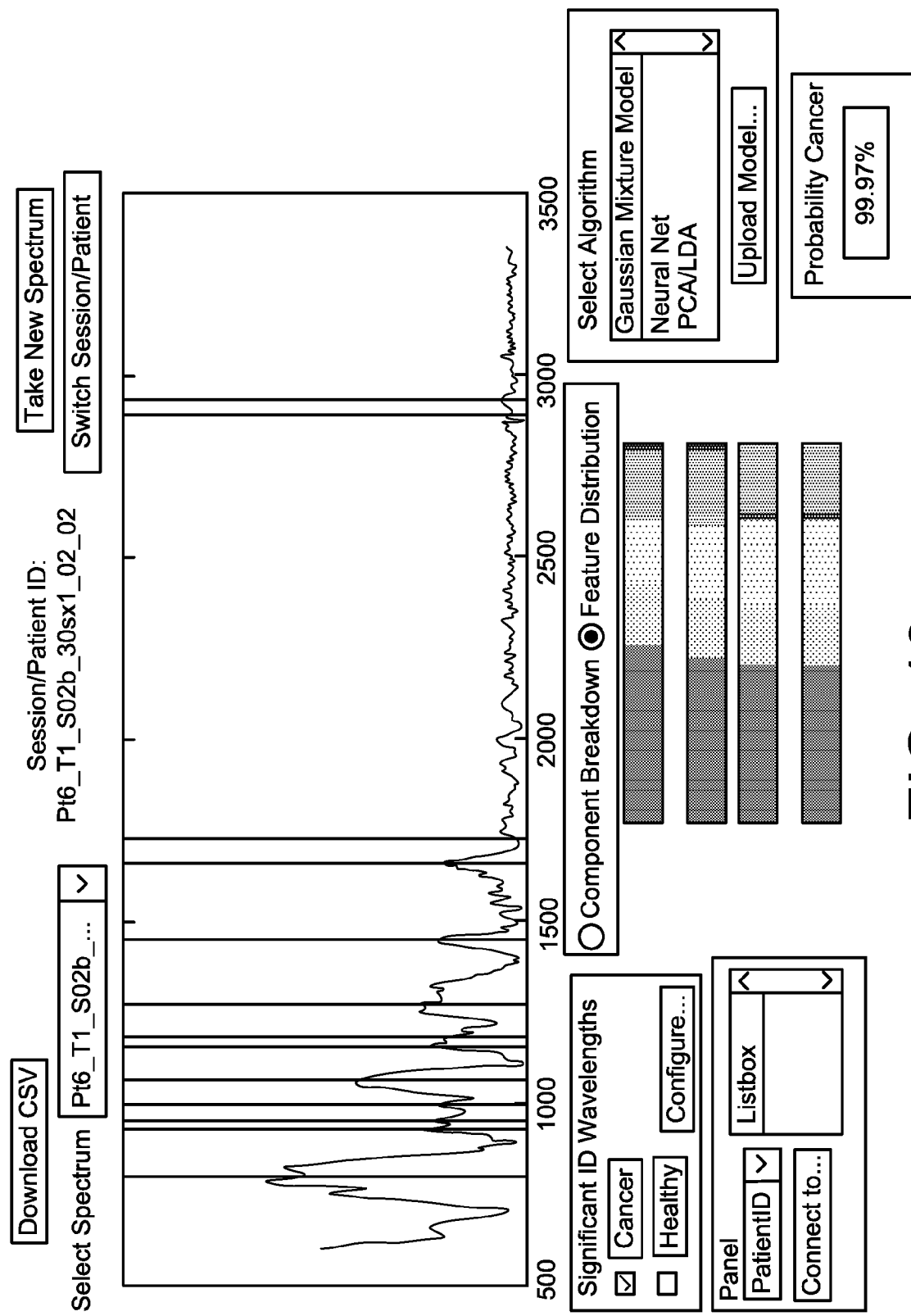

FIGS. 9 and 10 show non-limiting examples of GUIs that may be displayed or otherwise provided to a user. FIG. 9 shows a GUI related to diagnostics during surgery or other intervention. In the non-limiting example of FIG. 9, the GUI includes graphical information related to Lipids, Protein, DNA/RNA, and Hemoglobin levels, as well as user interfaces for starting and/or stopping a session and saving data related to a session. The GUI of FIG. 9 can be used to assist a user in identifying whether cancerous tissue is present in analyzed tissue. FIG. 10 shows a GUI that can be used in connection with a post-operation scenario. The GUI shown in FIG. 10 includes information and details that facilitate post-operative research for clinicians, such as pathologists, surgeons, and researchers.

In a subsequent step 520, the tissue that was indicated to be cancerous is ablated, such as via laser thermal ablation. The ablation of the cancerous tissue can occur immediately after the cancerous tissue is detected via the Raman spectra analysis. This can occur in situ such as via the trocar that was used to access the tissue. In an example implantation, a common (or same) energy source is used for both detection and ablation of the cancerous tissue. For example, the laser fiber 710 can be used to both obtain the Raman spectra and is then used to ablate the cancerous tissue, if present.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e g, mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, WiFI (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Thus, the spirit and scope of the appended claims should not be limited to the description of the embodiments contained herein.

The invention claimed is:

1. A method of detecting cancer in tissue, comprising: inserting a tissue access device into a tissue;
    collecting a sample tissue via the tissue access device;
    inserting a laser fiber into the sample tissue via the tissue access device;
    using laser Raman spectroscopy, via the laser fiber, to analyze the sample tissue and to generate a result;
    training at least one neural network across an entire spectral bandwidth and separately from selected portions of a high wavenumber and fingerprint regions that are sensitive to changes in nucleotide, protein, carbohydrate, or lipid cell components;
    employing the at least one neural network to differentiate between healthy tissue and cancerous tissue based on results of the laser Raman spectroscopy; and using the laser fiber to ablate cancerous tissue via the tissue access device.

2. The method of claim 1, wherein the result of the Raman spectroscopy is a unique biochemical signature of the sample tissue.

3. The method of claim 1, further comprising using gold nanoparticles to enhance a signal during Raman spectroscopy.

4. The method of claim 3, further comprising adsorbing at least one gold nanoparticle onto the sample tissue.

5. The method of claim 1, further comprising using Raman spectroscopy to analyze the tissue at wavelengths of 785 nanometers.

6. The method of claim 1, further comprising using Raman spectroscopy to analyze the tissue at wavelengths of 1064 nanometers.

7. The method of claim 1, wherein differentiating between healthy tissue and cancerous tissue comprises employing at least one neural network.

8. The method of claim 1, further comprising training the at least one neural network on Raman spectra with histopathology diagnostics that provide Bayesian estimates of the presence or absence of cancer in tissue.

9. The method of claim 1, wherein the at least one neural network generates a real time estimate of a Bayesian probability that the sample tissue contains cancer cells.

10. The method of claim 1, further comprising identifying cancerous tissue as a target for ablation based on results of the laser Raman spectroscopy.

11. The method of claim 10, further comprising immediately ablating the cancerous tissue after differentiating between healthy tissue and cancerous tissue.

12. The method of claim 11, wherein the tissue is ablated using a laser.

13. The method of claim 1, wherein the tissue access device is a trocar.

14. The method of claim 13, wherein the laser fiber is inserted into the sample tissue through a lumen of the trocar.

15. The method of claim 1, using a common energy source for both the laser Raman spectroscopy and ablation of cancerous tissue.

16. The method of claim 1, wherein the at least one neural network includes more than one neural network.

17. The method of claim 1, wherein the at least one neural network includes at least a first neural network trained on data across an entire spectral bandwidth and at least a second neural network trained on selected portions of a high wavenumber and fingerprint regions that are sensitive to changes in nucleotide, protein, carbohydrate, or lipid cell components.

* * * * *